(12) United States Patent
Nagare et al.

(10) Patent No.: US 9,066,860 B2
(45) Date of Patent: Jun. 30, 2015

(54) OIL-IN-WATER EMULSIFIED COMPOSITION

(75) Inventors: Yuko Nagare, Yokohama (JP); Yosuke Ikebe, Yokohama (JP); Momo Yabu, Yokohama (JP); Kazuhiro Yamaguchi, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 12/674,033

(22) PCT Filed: Sep. 29, 2009

(86) PCT No.: PCT/JP2009/004953
§ 371 (c)(1),
(2), (4) Date: Apr. 9, 2012

(87) PCT Pub. No.: WO2011/039790
PCT Pub. Date: Apr. 7, 2011

(65) Prior Publication Data
US 2012/0183480 A1    Jul. 19, 2012

(51) Int. Cl.
| A61K 8/06 | (2006.01) |
| A61K 8/26 | (2006.01) |
| A61K 8/35 | (2006.01) |
| A61K 8/36 | (2006.01) |
| A61K 8/40 | (2006.01) |
| A61K 8/41 | (2006.01) |
| A61K 8/49 | (2006.01) |
| A61Q 17/04 | (2006.01) |

(52) U.S. Cl.
CPC . *A61K 8/06* (2013.01); *A61K 8/062* (2013.01); *A61K 8/26* (2013.01); *A61K 8/35* (2013.01); *A61K 8/361* (2013.01); *A61K 8/40* (2013.01); *A61K 8/411* (2013.01); *A61K 8/4966* (2013.01); *A61Q 17/04* (2013.01)

(58) Field of Classification Search
CPC ....... A61K 8/062; A61K 8/35; A61K 8/4966; A61Q 17/04
See application file for complete search history.

(56) References Cited

U.S. PATENT DOCUMENTS

| 6,517,816 B1 * | 2/2003 | Gonzalez et al. ........ 424/59 |
| 2001/0021375 A1 * | 9/2001 | Hossel et al. ........ 424/59 |
| 2006/0008429 A1 | 1/2006 | Candau |
| 2008/0089852 A1 | 4/2008 | Hotz et al. |
| 2008/0247975 A1 * | 10/2008 | Dueva-Koganov et al. .... 424/59 |
| 2009/0016971 A1 | 1/2009 | Gaudry et al. |
| 2009/0196894 A1 * | 8/2009 | Ehlis et al. ........ 424/401 |

FOREIGN PATENT DOCUMENTS

| DE | 10 2007 024342 | 11/2008 |
| JP | 2008-162930 A | 7/2008 |
| JP | 2008-266252 A | 11/2008 |
| JP | 2009-062311 A | 3/2009 |
| JP | 2008-518988 A | 5/2009 |
| JP | 2009-062327 A | 5/2009 |
| JP | 2009-102281 A | 5/2009 |
| WO | 2006048159 | 5/2006 |
| WO | WO 2006048159 A1 * | 5/2006 |
| WO | WO 2007017179 A1 * | 2/2007 |
| WO | WO 2008/119428 | 10/2008 |

OTHER PUBLICATIONS

PCT/JP2009/004953, International Preliinary Report on Patentability mailed Apr. 11, 2012, 7 pages.
Russian Appln. Serial No. 2010110155/15, Office Action dated Mar. 1, 2013, 4 pages—Russian, 3 pages—English.
Database GNPD (online), Mintel; Apr. 2, 2007, "SPF 30 Continuous Spray Sunscreen", accession No. 682105.
Database GNPD (online), Mintel; Jul. 1, 2009, "Extra Care Non-Greasy Sunscreen SPF 45+", accession No. 1138768.
Database GNPD (online), Mintel; Apr. 1, 2010, "SPF 50+ Quenching Fluid", XP002733636, accession No. 1339372.
EP 09 84 9982—European Search Report dated from Jan. 15, 2015, 5 pages.

* cited by examiner

*Primary Examiner* — Sean Basquill
*Assistant Examiner* — Andrew S Rosenthal
(74) *Attorney, Agent, or Firm* — Andrew F. Young, Esq.; Lackenbach Siegel, LLP

(57) ABSTRACT

The present invention is an oil-in-water emulsified composition and a sunscreen cosmetic characteristically comprising the following (a)-(j):
(a) Octocrylene
(b) Bis ethylhexyloxyphenol methoxyphenyl triazine
(c) Hexyl diethylaminohydroxybenzoylbenzoate
(d) 4-tert-butyl-4'-methoxybenzoylmethane
(e) Water soluble polymer
(f) Water-swelling clay mineral
(g) Oil component having IOB of 0.05 or more
(h) Higher fatty acid
(i) Surfactant
(j) Water
The object of the present invention is to provide a sunscreen cosmetic that manifests a superior ultraviolet absorption effect and is superior in terms of the emulsification stability and the sensation during use.

14 Claims, 1 Drawing Sheet

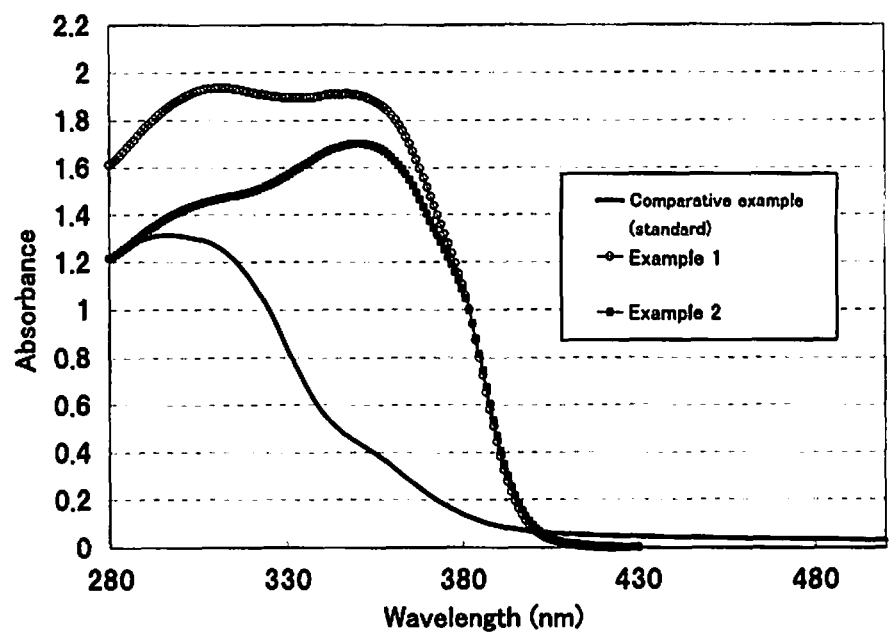

OIL-IN-WATER EMULSIFIED COMPOSITION

TECHNICAL FIELD

The present invention relates to an oil-in-water emulsified composition. More specifically, it relates to an oil-in-water emulsified composition that contains specific ultraviolet absorbent and polar oil. The oil-in-water emulsified composition of the present invention is preferably used as a sunscreen cosmetic.

BACKGROUND ART

Important ultraviolet wavelength regions absorbed by sunscreen cosmetics are the UV-A region (320-400 nm) and UV-B region (290-320 nm). It was believed that the ultraviolet light in the UV-A region (320-400 nm) darkened the skin but it would not cause sunburn and accelerate aging of the skin as the ultraviolet light in the UV-B region (290-320 nm) would. However, in recent years, it has been made clear that, whereas the ultraviolet light in the UV-B region (290-320 nm) only reaches the surface part of the skin, the ultraviolet light in the UV-A region (320-400 nm) reaches the deeper part of the skin and induces not only skin aging but also skin cancer.

Ultraviolet absorbents for cosmetics that have been used up to the present are structurally categorized into (1) benzoic acid derivatives, (2) cinnamic acid derivatives, (3) benzophenone derivatives, (4) dibenzoylmethane derivatives, and (5) salicylic acid derivatives. In recent years, ultraviolet absorbents of (2) and (4) are frequently used.

However, the ultraviolet absorbents listed above each have problems from a practical point of view. For example, 2-ethylhexyl-p-dimethylaminobenzoate, an example of (1) benzoic acid derivatives, is a transparent liquid and has the advantage of being easy to handle; however, it and its derivatives are questionable in terms of safety and therefore are not used in recent years. Also, its peak absorption wavelength is near 290 nm and it absorbs only the ultraviolet light in the UV-B region.

Among (2) cinnamic acid derivatives, 2-ethylhexyl p-methoxycinnamate is the most frequently used ultraviolet absorbent in the sun care cosmetics currently available commercially. Its maximum absorption wavelength is near 310 nm and its absorption region does not reach the UV-A region. Also, sunlight degenerates it and therefore it has problems with staining and also with instability of the ultraviolet protection effect.

As for (3) benzophenone derivatives, 2-hydroxy-4-methoxybenzophenone, for example, absorbs both the UV-A and UV-B regions and exhibits relatively good solubility in external preparation base agents; however, its maximum absorption wavelength is rather close to the UV-B region and the absorbance is not very high. Also, in recent years, its basic structural skeleton (benzophenone) has been implicated as an environmental hormone and its use has been avoided.

Among (4) dibenzoylmethane derivatives, 4-tert-butyl-4'-methoxybenzoylmethane is frequently used for external preparations. Its maximum absorbance is at around 360 nm and the absorbance level is high, and therefore it is a superior ultraviolet absorbent in the UV-A region. However, it has a problem in photostability, and it exhibits poor compatibility with oil components in external preparations and therefore only a small amount can be added.

Among (5) salicylic acid derivatives, octyl salicylate is used. It has a maximum absorption wavelength in the UV-B region, and it is in an oil form and exhibits superior compatibility with paraffin oil and such; however, since its absorbance is low, it is not put to practical use much.

Therefore, 2-ethylhexyl-p-methoxycinnamate from (2) is often used for the UV-B region and 4-tert-butyl-4'-methoxybenzoylmethane from (4) is often used for the UV-A region. In recent years in particular, there is an increasing demand for ultraviolet absorption in the UV-A region.

Some ultraviolet absorbents are sticky, which can be a significant problem when they are blended into sunscreen cosmetics, for which the sensation during use is deemed important. That is, when the blend ratio of the ultraviolet absorbent is increased for the purpose of a higher ultraviolet absorption effect, the sensation during use dramatically worsens. Therefore, there are cases where the desired blend ratio cannot be achieved with the desired ultraviolet absorbent.

Also, generally, a practice of blending multiple ultraviolet absorbents into a sunscreen cosmetic is done for the purpose of securing a broad absorption range.

However, in the case of sunscreen cosmetics containing an ultraviolet absorbent, the sensation during use may decrease. Since a superior sensation during use is an important element strongly required for cosmetics, the practice of blending in multiple ultraviolet absorbents, particularly 3, 4 or more different types, is not usually done, even for the purpose of securing a broad absorption range.

Meanwhile, dibenzoylmethane derivatives, which are blended into cosmetics as ultraviolet absorbents, lose some of their UV absorption capacity when exposed to ultraviolet light. Technology that uses both a benzoylmethane derivative and α-cyano-β,β-diphenylacrylate, which is another ultraviolet absorbent, has been developed in order to control this phenomenon and secure the photostability (Patent Document 1).

Also, in the case of a cosmetic that uses both ultraviolet absorbents, a 1,3,5-triazine derivative and a dibenzoylmethane derivative, the 1,3,5-triazine derivative chemically degrades significantly by ultraviolet irradiation under the presence of 4-tert-butyl-4'-methoxydibenzoylmethane. Therefore, technology that additionally uses α-cyano-β,β-diphenylacrylate to secure photostability of the 1,3,5-triazine derivative and dibenzoylmethane derivative has been developed (Patent Document 2).

However, there is a problem in the technology that secures photostability of the ultraviolet absorbents themselves by using multiple ultraviolet absorbents. Because many of the solid ultraviolet absorbents have low compatibility with, and are hardly soluble in, the oil components that are the base agent of the cosmetics, therefore, if they are to be stably blended into cosmetics, a large amount of specific oil components having superior compatibility needs to be added. The presence of specific oil components in large quantities would be a cause of a reduction in the stability of the cosmetic (particularly the emulsification stability of oil-in-water emulsified cosmetics) and a reduction in the sensation during use.

As described thus far, using multiple ultraviolet absorbents together is a cause for a reduction in the stability and in the sensation during use of the cosmetic, and therefore it is not a usual practice to blend multiple (particularly four types or more) different ultraviolet absorbents into a sunscreen cosmetic.

Also, there are few reports on the emulsification stability (particularly the dissolution stability of the ultraviolet absorbents at lower temperatures) in cases where four or more ultraviolet absorbents are blended into an oil-in-water emulsified composition.

PRIOR ART DOCUMENTS

Patent Documents

Patent Citation 1: Japanese Patent No. 2975682
Patent Citation 2: Japanese Patent No. 3714632

DISCLOSURE OF INVENTION

Technical Problem

In order to obtain a high ultraviolet protection in the UV-A region and the UV-B region, it is necessary to blend in ultraviolet absorbents in such a way that the UV-A absorbents and the UV-B absorbents are in a good balance.

However, since many common UV-A absorbents are hardly soluble, a large amount of a highly polar oil component needs to be blended in to dissolve them, which has made it difficult to obtain a stable oil-in-water emulsified composition base agent.

Also, there were problems such as a reduction in the emulsification stability and in the sensation during use when attempts were made to manufacture sunscreen cosmetics that were oil-in-water emulsified compositions containing four or more ultraviolet absorbents.

In view of the aforementioned problem, the inventors conducted earnest research on sunscreen cosmetics that have a superior ultraviolet absorption effect and also superior emulsification stability and sensation during use, and discovered that oil-in-water emulsified compositions and sunscreen cosmetics that manifest a superior ultraviolet protection effect and are superior in terms of the emulsification stability and the sensation during use could be obtained by blending in a combination of four specific ultraviolet absorbents and specific cosmetic ingredients, thus completing the present invention.

The object of the present invention is to provide an oil-in-water emulsified composition and a sunscreen cosmetic that manifest a superior ultraviolet absorption effect and are superior in terms of the emulsification stability and the sensation during use.

Technical Solution

That is, the present invention provides an oil-in-water emulsified composition characteristically comprising the following (a)-(j).
(a) Octocrylene
(b) Bis ethylhexyloxyphenol methoxyphenyl triazine
(c) Hexyl diethylaminohydroxybenzoylbenzoate
(d) 4-tert-butyl-4'-methoxybenzoylmethane
(e) Water soluble polymer
(f) Water-swelling clay mineral
(g) Oil component having IOB of 0.05 or more
(h) Higher fatty acid
(i) Surfactant
(j) Water Also, the present invention provides the aforementioned oil-in-water emulsified composition wherein the blend ratio of said "(f) water-swelling mineral" is 0.01-4 mass % of the total amount of the aforementioned oil-in-water emulsified composition.

Furthermore, the present invention provides the aforementioned oil-in-water emulsified composition wherein the blend ratio of said "(g) Oil component having IOB of 0.05 or more" is 20-75 mass % of the oil phase.

Also, the present invention provides the aforementioned oil-in-water emulsified composition wherein said "(e) Water soluble polymer" is a polysaccharide.

Furthermore, the present invention provides the aforementioned oil-in-water emulsified composition wherein said "(g) Oil component having IOB of 0.05 or more" is an ester oil.

Also, the present invention provides the aforementioned oil-in-water emulsified composition wherein the total blend ratio of (a) Octocrylene, (b) Bis ethylhexyloxyphenol methoxyphenyl triazine, (c) Hexyl diethylaminohydroxybenzoylbenzoate, and (d) 4-tert-butyl-4'-methoxybenzoylmethane is 10-25 mass % of the total amount of the oil-in-water emulsified composition.

Furthermore, the present invention provides a sunscreen cosmetic composed of the aforementioned oil-in-water emulsified composition.

Advantageous Effects

The oil-in-water emulsified composition of the present invention manifests a superior ultraviolet protection effect and is superior in terms of the emulsification stability and the sensation during use, and therefore a superior sunscreen cosmetic can be provided.

BRIEF DESCRIPTION OF DRAWINGS

FIG. 1 It shows absorbance curves of Examples and Comparative examples.

BEST MODE FOR CARRYING OUT THE INVENTION

The present invention is described in detail below.
"Ultraviolet Absorbent"

The four types of ultraviolet absorbents that are blended into the present invention are (a) Octocrylene, (b) Bis ethylhexyloxyphenol methoxyphenyl triazine, (c) Hexyl diethylaminohydroxybenzoylbenzoate, and (d) 4-tert-butyl-4'-methoxybenzoylmethane (t-butylmethoxydibenzoylmethane). Each of them is a prior art ultraviolet absorbent.

"(a) Octocrylene" (2-ethylhexyl 2-cyano-3,3-diphenylacrylate) is commercially available as for example, "PARSOL™ 340" (from DSM Nutritional Products).

"(b) Bis ethylhexyloxyphenol methoxyphenyl triazine" is commercially available as, for example, "TINOSORB™ S" (from Ciba Specialty Chemicals).

"(c) Hexyl diethylaminohydroxybenzoylbenzoate" is commercially available as, for example, "UVINUL™ A plus granular" (from BASF JAPAN).

"(d) 4-tert-butyl-4'-methoxybenzoylmethane" is commercially available as, for example, "PARSOL™ 1789" (from DSM Nutritional Products).

The blend ratios of the aforementioned four types of ultraviolet absorbents are determined as appropriate for the product. The total amount of the four types to be blended in is usually 1-40 mass %, preferably 5-30 mass %, and more preferably 10-25 mass %, of the total amount of the oil-in-water emulsified composition. If their total amount is less than 1 mass %, then not enough ultraviolet absorbent absorption effect is manifested; if it is more than 40 mass %, then stickiness arises.

"Water Soluble Polymer"

Examples of "(e) Water soluble polymer" used in the present invention include polysaccharides such as xanthan gum, carrageenan, pectin, mannan, curdlan, chondroitin sulfuric acid, starch, galactan, dermatan sulfate, glycogen, gum arabic, heparan sulfate, hyaluronic acid, sodium hyaluronate, traganth gum, keratan sulfate, chondroitin, mucoitin sulfuric acid, hydroxyethyl guar gum, carboxymethyl guar gum, guar gum, carob gum, dextran, kerato sulfate, locustbean gum, succinoglucane, charonic acid, chitin, chitosan, carboxymethyl chitin, quince seed, starch (rice, corn, potato, wheat), glycyrrhizin, pullulan, and agar.

Examples of the cellulosic polymers include methyl cellulose, ethyl cellulose, methylhydroxypropyl cellulose, hydroxyethyl cellulose, cellulose sodium sulfate, hydroxypropyl cellulose, carboxymethyl-cellulose, sodium carboxymethyl cellulose, crystalline cellulose, and cellulose powder.

Examples of the vinyl polymer include polyvinyl alcohol, polyvinylmethyl ether, polyvinyl pyrrolidone, and carboxyvinyl polymer.

Examples of the acrylic polymer include sodium polyacrylate, polyethylacrylate, and polyacrylamide.

The blend ratio of the water soluble polymer is usually 0.01-5 mass %, preferably 0.01-1 mass %, and more preferably 0.1-0.5 mass %, of the total amount of the oil-in-water emulsified composition. If the blend ratio is less than 0.01 mass %, then the emulsification stability of the composition becomes poor, and if it is over 5 mass %, then the sensation during use is sticky.

"Water-Swelling Clay Mineral"

"(f) Water-swelling clay mineral" used in the present invention is a layered silicate mineral that belongs to the smectite group; common examples include montmorillonite, beidellite, nontronite, saponite, hectorite, and bentonite. They can be either natural or synthesized. The commercial products include KUNIPIA™, Smectone (both from Kunimine Industries Co., Ltd.), LAPONITET™ (from Laporte Industries, Inc.), synthetic sodium type fluoride bearing phlogopite (SUBMICA™ E from Daito Kasei Kogyo Co., Ltd.), and VEEGUM™ Ultra Granules (from R. T. Vanderbilt Company, Inc.). Among these, KUNIPIA™ and Smectone are particularly preferable.

The blend ratio of the water-swelling clay mineral is usually 0.01-4 mass %, preferably 0.01-2 mass %, and more preferably 0.01-1 mass %, of the total amount of the oil-in-water emulsified composition. If the blend ratio is less than 0.01 mass %, then the emulsification stability of the composition becomes poor, and if it is over 4 mass %, then the spreading on the skin becomes poor.

"Oil Component Having IOB of 0.05 or More"

The oil component used in the present invention is a polar oil having IOB of 0.05 or more, preferably an ester oil having IOB of 0.05-0.8. Specific examples include isononyl isononanoate, isopropyl myristate, cetyl hexanoate, octyl dodecyl myristate, isopropyl palmitate, butyl stearate, hexyl laurate, myristil myristate, decyl oleate, hexyldecyl dimethyloctanoate, cetyl lactate, myristil lactate, lanolin acetate, isocetyl stearate, isocetyl isostearate, cholesteryl 12-hydroxystearate, ethylene glycol di-2-ethylhexanoate, dipentaerythritol fatty acid ester, N-alkyl glycol monoisostearate, neopentyl glycol dicaprate, diisostearyl malate, glycerin di-2-heptylundecanoate, trimethylolpropane tri-2-ethylhexanoate, trimethylolpropane triisostearate, pentaerythritol tetra-2-ethylhexanoate, glycerin tri-2-ethylhexanoate, trimethylolpropane triisostearate, cetyl 2-ethyl hexanoate, 2-ethylhexyl palmitate, diethylhexyl naphthalenedicarboxylate, alkyl benzoate (12-15 carbon atoms), cetearyl isononanoate, glycerin tri-(caprylate/caprate), butylene glycol (dicaprylate/caprate), glycerin trimyristate, tri-2-heptyl undecanoate glyceride, castor oil fatty acid methyl ester, oleyl oleate, ceto-stearyl alcohol, aceto glyceride, 2-heptyl undecyl palmitate, diisobutyl adipate, 2-octyldodecyl N-lauroyl-L-glutamate, di-2-heptyl undecyl adipate, ethyl laurate, di-2-ethylhexyl sebacate, 2-hexyl decyl myristate, 2-hexyl decyl palmitate, 2-hexyl decyl adipate, diisopropyl sebacate, 2-ethylhexyl succinate, ethyl acetate, butyl acetate, amyl acetate, triethyl citrate, 2-ethylhexyl para-methoxycinnamate, and tripropylene glycol dipivalate. Among these, isononyl isononanoate, glyceryl 2-ethylhexanoate, cetyl 2-ethylhexanoate, and diisopropyl sebacate are particularly preferable.

IOB is an acronym of Inorganic/Organic Balance, which indicates the ratio of the inorganic value to the organic value and is an indicator of the degree of polarization of organic compounds. The IOB value is specifically expressed as "IOB value=Inorganic value/Organic value." Regarding the "inorganic value" and "organic value" here, each atom or functional group in a molecule is assigned an "inorganic value" and "organic value", such as an "organic value" of 20 for one carbon atom and an "inorganic value" of 100 for a hydroxide group, and the IOB value of an organic compound can be calculated by summing up the "inorganic values" and "organic values" of all the atoms and functional groups in said organic compound (refer to, for example, "Kagaku no Ryoiki (Areas of Chemistry)" by Fujita, 1957, volume 11, issue 10, p719-725).

The blend ratio of the oil component having IOB of 0.05 or more is usually 1-70 mass %, preferably 3-50 mass %, and more preferably 5-30 mass %, of the total amount of the oil-in-water emulsified composition.

Also, it is preferable that the ratio of the oil component having IOB of 0.05 or more in the oil phase be 20-75 mass %. The oil phase is the oil-based ingredients including ultraviolet absorbents (a)-(d) and the surfactant.

"Higher Fatty Acid"

In the present invention, in terms of the emulsification stability of the oil-in-water emulsified composition, it is preferable to blend in a "(h) Higher fatty acid." Specific examples include lauric acid, myristic acid, palmitic acid, stearic acid, behenic acid, oleic acid, undecylenic acid, tall oil, isostearic acid, linolic acid, and linoleic acid. Among these, it is preferable to use stearic acid and behenic acid. It is acceptable for the higher fatty acid to form higher fatty acid soap in the oil-in-water emulsified composition.

In the present invention, the blend ratio of the higher fatty acid is usually 0.1-10 mass %, preferably 0.1-5 mass % of the total amount of the oil-in-water emulsified composition. More preferably it is 0.5-2 mass %.

"Surfactant"

In the present invention, "(i) Surfactant" is blended in to prepare the oil-in-water emulsified composition. The surfactant used in the present invention is determined as appropriate, but it is preferable to use a lipophilic nonionic surfactant and/or hydrophilic nonionic surfactant. Examples of the surfactant that can be used in the present invention are shown below.

Examples of the hydrophilic nonionic surfactant include POE alkyl ether, POE alkyl phenyl ether, POE-POP alkyl ether, POE fatty acid ester, POE fatty acid ester, POE sorbitan fatty acid ester, POE glycerin fatty acid ester, POE castor oil or hydrogenated castor oil derivatives, POE beeswax-lanolin derivatives, alkanolamide, POE propylene glycol fatty acid ester, POE alkylamine, POE fatty acid amide, sucrose fatty acid ester, and polyether-modified silicone. These can be used independently or in combinations of two or more.

"POE" stands for polyoxyethylene and "POP" stands for polyoxypropylene; they may be referred to as such below.

Among the aforementioned hydrophilic nonionic surfactants, ethylene oxide adduct type nonionic surfactants having a HLB of 8 or more are particularly preferable; examples include POE (10-50 mole) phytosterol ether, POE (10-50 mole) dihydrocholesterol ether, POE (10-50 mole) 2-octyldodecyl ether, POE (10-50 mole) decyltetradecyl ether, POE (10-50 mole) oleyl ether, POE (10-50 mole) cetyl ether, POE (5-30 mole) POP (5-30 mole) 2-decyltetradecyl ether, POE (10-50 mole) POP (2-30 mole) cetyl ether, POE (20-60 mole) sorbitan monooleate, POE (10-60 mole) sorbitan monoisostearate, POE (10-80 mole) glyceryl monoisostearate, POE (10-30 mole) glyceryl monostearate, and POE (20-100) hydrogenated castor oil derivatives.

Examples of the lipophilic nonionic surfactant include sorbitan monooleate, sorbitan sesquioleate, sorbitan trioleate, sorbitan monoisostearate, sorbitan sesquiisostearate, glyceryl monooleate, glyceryl monoisostearate, glyceryl diisostearate, glyceryl monoerucate, diglycerin monooleate, diglycerin dioleate, diglycerin monoisostearate, diglycerin diisostearate, decaglycerin pentaoleate, decaglycerin pentaisostearate, decaglycerin decaoleate, decaglycerin decaisostearate, sucrose monooleate, POE (2 mole) monooleate, POE (6 mole) diisostearate, and POE (3-10 mole) castor oil derivatives.

The blend ratio of the surfactant is determined as appropriate; it is usually 0.1-10 mass %, preferably 0.1-5 mass %, and more preferably 0.5-3 mass %, of the total amount of the oil-in-water emulsified composition.

"Water"

In the present invention, the blend ratio of "(j) Water" is preferably 50-90 mass % of the total amount of the oil-in-water emulsified composition. Water-based ingredients such as a "(e) Water soluble polymer" and "(f) Water-swelling clay mineral" are dissolved in water to form the water phase.

The oil-in-water emulsified composition of the present invention can be prepared using a common method by suitably blending the aforementioned essential ingredients with, as necessary, additional other components that are normally used in cosmetics, such as powder components, liquid fats and oils, solid fats and oils, waxes, hydrocarbons, higher fatty acids, higher alcohols, ester oils, silicone oils, anionic surfactants, cationic surfactants, amphoteric surfactants, nonionic surfactants, humectants, thickeners, coating agents, sequestering agents, lower alcohols, polyhydric alcohols, sugars, amino acids, organic amines, polymer emulsions, pH adjusting agents, skin nutrients, vitamins, antioxidants, antioxidation assistants, and perfumes.

The oil-in-water emulsified composition of the present invention is preferably used as a sunscreen cosmetic. Preferable products are W/O emulsion sunscreen creams, sunscreen emulsions, sunscreen lotions, etc.

EXAMPLES

The present invention is described further in detail below by referring to Examples. The present invention is not limited to these Examples. The blend ratios in Examples are in mass % (mass-percentage) units unless specified otherwise.

A (water phase) and B (oil phase) in the following Table 1 and Table 2 were heated up to 70° C. and dissolved completely. A was added to B, followed by emulsification with an emulsifier, to prepare the oil-in-water emulsified composition (cream-like sunscreen cosmetic).

'Emulsification Stability'

The obtained composition was sealed into a 50 ml screw tube and stored for four weeks at 50° C.; the emulsification stability was then evaluated based on the external appearance.

<Evaluation>

One layer state is maintained: o
Separated: x

As a result, regarding Table 1, separation occurred in Comparative examples 1 and 2, which had only "(e) Water soluble polymer" (xanthan gum) where as Example 1, which had a small amount of "(f) Water-swelling clay mineral" (smectite) exhibited good stability without spoiling the sensation during use.

Regarding Table 2, Comparative example 3, which had only "(e) Water soluble polymer" (xanthan gum), exhibited separation. Furthermore, Comparative examples 4-5, which had xanthan gum as one "(e) Water soluble polymer" and succinoglucane as another "(e) Water soluble polymer", exhibited separation and also the sensation during use was spoiled, too. On the contrary, Examples 2-5, which had "(f) Water-swelling clay mineral" (bentonite), exhibited good stability. Of these, Examples 2-3 gave a good sensation during use as well.

"Sensation During Use"

<Evaluation>

A panel of ten female specialists actually applied the samples on the skin and evaluated the spreading (lightness) based on the following standards.

o: Eight or more judged that it spread lightly.
Δ: Three to seven judged that it spread lightly.
x: Two or fewer judged that it spread lightly.

TABLE 1

|  |  | Comparative example 1 | Comparative example 2 | Example 1 |
|---|---|---|---|---|
| Water phase | (j) Ion-exchanged water | Balance | Balance | Balance |
|  | 95 ethyl alcohol, synthesized | 5.0 | 5.0 | 5.0 |
|  | 1,3-butylene glycol | 5.0 | 5.0 | 5.0 |
|  | Glycerin | 5.0 | 5.0 | 5.0 |
|  | (e) Xanthan gum | 0.1 | 0.3 | 0.1 |
|  | (f) Smectone (from Kunimine Industries Co., Ltd.) | — | — | 0.1 |
|  | Triethanolamine | 0.25 | 0.25 | 0.25 |
|  | EDTA-3Na•2H2O | 0.1 | 0.1 | 0.1 |
|  | Phenoxy ethanol | 0.5 | 0.5 | 0.5 |
| Oil phase | (i) Glyceryl monostearate | 1.5 | 1.5 | 1.5 |
|  | (i) POE glyceryl isostearate | 1.5 | 1.5 | 1.5 |
|  | (h) Behenic acid | 1 | 1 | 1 |
|  | Polyvinylpyrrolidone/eicosene copolymer | 2.0 | 2.0 | 2.0 |
|  | Batyl alcohol | 0.5 | 0.5 | 0.5 |
|  | Behenyl alcohol | 1 | 1 | 1 |
|  | (g) Isononyl isononanoate | 10 | 10 | 10 |

TABLE 1-continued

|  |  | Comparative example 1 | Comparative example 2 | Example 1 |
|---|---|---|---|---|
|  | (g) Glyceryl tri-2-ethylhexanoate | 5 | 5 | 5 |
|  | (a) Octocrylene | 10 | 10 | 10 |
|  | (b) Bis ethylhexyloxyphenol methoxyphenyl triazine | 3 | 3 | 3 |
|  | (c) Hexyl diethylaminohydroxybenzoylbenzoate | 3 | 3 | 3 |
|  | (d) 4-tert-butyl-4'-methoxydibenzoylmethane | 3 | 3 | 3 |
|  | Dimethicodiethyl benzal malonate | 5 | 5 | 5 |
|  | Perfume | Appropriate amount | Appropriate amount | Appropriate amount |
|  | Total | 100 | 100 | 100 |
| Evaluation | Emulsification stability | x | x | ○ |
|  | Sensation during use | ○ | ○ | ○ |

TABLE 2

|  |  | Comparative example 3 | Comparative example 4 | Comparative example 5 | Example 2 | Example 3 | Example 4 | Example 5 |
|---|---|---|---|---|---|---|---|---|
| Water phase | (j) Ion-exchanged water | Balance | Balance | Balance | Balance | Balance | Balance | Balance |
|  | 95 ethyl alcohol, synthesized | 5.0 | 5.0 | 5.0 | 5.0 | 5.0 | 5.0 | 5.0 |
|  | 1,3-butylene glycol | 5.0 | 5.0 | 5.0 | 5.0 | 5.0 | 5.0 | 5.0 |
|  | Glycerin | 5.0 | 5.0 | 5.0 | 5.0 | 5.0 | 5.0 | 5.0 |
|  | (e) Xanthan gun | 0.1 | 0.1 | 0.1 | 0.1 | 0.1 | 0.1 | 0.1 |
|  | (e) Succinoglucane | — | 0.3 | — | — | — | — | — |
|  | (e) Carbomer | — | — | 0.3 | — | — | — | — |
|  | (f) Bentonite | — | — | — | 0.1 | 0.5 | 1 | 2 |
|  | Triethanolamine | 0.25 | 0.25 | 0.45 | 0.25 | 0.25 | 0.25 | 0.25 |
|  | EDTA-3Na•2H2O | 0.1 | 0.1 | 0.1 | 0.1 | 0.1 | 0.1 | 0.1 |
|  | Phenoxy ethanol | 0.5 | 0.5 | 0.5 | 0.5 | 0.5 | 0.5 | 0.5 |
| Oil phase | (i) Glyceryl monostearate | 1.5 | 1.5 | 1.5 | 1.5 | 1.5 | 1.5 | 1.5 |
|  | (i) POE glyceryl isostearate | 1.5 | 1.5 | 1.5 | 1.5 | 1.5 | 1.5 | 1.5 |
|  | (h) Behenic acid | 1 | 1 | 1 | 1 | 1 | 1 | 1 |
|  | Polyvinylpyrrolidone/ eicosene copolymer | 2.0 | 2.0 | 2.0 | 2.0 | 2.0 | 2.0 | 2.0 |
|  | Batyl alcohol | 0.5 | 0.5 | 0.5 | 0.5 | 0.5 | 0.5 | 0.5 |
|  | Behenyl alcohol | 1 | 1 | 1 | 1 | 1 | 1 | 1 |
|  | (g) Isononyl isononanoate | 10 | 10 | 10 | 10 | 10 | 10 | 10 |
|  | (g) Glyceryl tri-2-ethylhexanoate | 5 | 5 | 5 | 5 | 5 | 5 | 5 |
|  | (a) Octocrylene | 5 | 5 | 5 | 5 | 5 | 5 | 5 |
|  | (b) Bis ethylhexyloxyphenol methoxyphenyl triazine | 3 | 3 | 3 | 3 | 3 | 3 | 3 |
|  | (c) Hexyl diethylamino hydroxybenzoylbenzoate | 3 | 3 | 3 | 3 | 3 | 3 | 3 |
|  | (d) 4-tert-butyl-4'-methoxydibenzoylmethane | 3 | 3 | 3 | 3 | 3 | 3 | 3 |
|  | Perfume | Appropriate amount | Appropriate amount | Appropriate amount | Appropriate amount | Appropriate amount | Appropriate amount | Appropriate amount |
|  | Total | 100 | 100 | 100 | 100 | 100 | 100 | 100 |
| Evaluation | Stability | x | x | x | ○ | ○ | ○ | ○ |
|  | Sensation during use | ○ | x | x | ○ | ○ | ○ | Δ |

"Ultraviolet Absorption Effect"

50 uL of samples from Examples 1 and 2 and Comparative example 6 were applied uniformly on a nylon membrane (5×5 cm) at a density of 2 mg/cm²; after this was allowed to stand for 15 minutes, a spectrophotometer (U-4100 from Hitachi, Ltd.) was used to measure the absorbance. The results are shown in FIG. 1. FIG. 1 indicates that the UV absorption of Examples 1 and 2 are far superior to Comparative example 6. The SPF (Sun Protection Factor) and PA (Protection Grade of UVA) of the Comparative example are 34 and +++, respectively; therefore, the sunscreen cosmetics of Examples 1 and 2 have a SPF of 30 or higher and a PA of +++ or hither, which confirms the fact that they have a high SPF and PA.

The formulation for Comparative example 6 is shown in Table 3. Comparative example 6 is a standard formulation for comparing the ultraviolet absorption effect and this formulation has a superior ultraviolet absorption effect, i.e. SPF30 and PA+++.

TABLE 3

|  | Comparative example 6 |
|---|---|
| (j) Water | Balance |
| Ethanol | 7 |
| Glycerin | 2 |

TABLE 3-continued

|  | Comparative example 6 |
| --- | --- |
| Carbomer | 0.3 |
| (e) Xanthan gum | 0.2 |
| (i) Polyoxyethylene hydrogenated castor oil | 1.5 |
| (i) Polyether-modified silicone | 1 |
| Decamethylcyclopentasiloxane | 12 |
| Isostearic acid | 1 |
| (g) Isononyl isononanoate | 2 |
| Titanium oxide | 5 |
| Octyl-p-methoxycinnamate | 5 |
| (a) Octocrylene | 2 |
| (c) Hexyl diethylaminohydroxybenzoylbenzoate | 0.5 |
| EDTA-3Na | 0.5 |
| Phenoxy ethanol | 0.5 |

"Solubility of the Ultraviolet Absorbent"

Solubility of (b) Bis ethylhexyloxyphenol methoxyphenyl triazine, (c) Hexyl diethylaminohydroxybenzoylbenzoate, and (d) 4-tert-butyl-4'-methoxybenzoylmethane in various oil components at 0° C., at a concentration of 1.5 mass %, was tested.

As a result, precipitation was observed for the oil components having IOB of 0, but not for the oil components having IOB of 0.05 or more. That is, it is demonstrated that the ultraviolet absorbents of (b)-(d) have excellent solubility in oil components having IOB of 0.05 or more. Therefore, the present invention provides stable oil-in-water emulsified compositions that do not precipitate the ultraviolet absorbent.

TABLE 4

|  | Syncelane | Liquid petrolatum | Octocrylene | Cetyl 2-ethylhexanoate | Glyceryl 2-ethylhexanoate | Diisopropyl sebacate |
| --- | --- | --- | --- | --- | --- | --- |
| IOB value | 0 | 0 | 0.33 | 0.13 | 0.35 | 0.4 |
| Bis ethylhexyloxyphenol methoxyphenyl triazine | x | x | ○ | ○ | ○ | ○ |
| Hexyl diethylaminohydroxybenzoylbenzoate | x | x | ○ | ○ | ○ | ○ |
| 4-tert-butyl-4'-methoxydibenzoylmethane | x | x | ○ | ○ | ○ | ○ |

(○: Precipitation was not observed at 0° C.
x: Precipitation was observed at 0° C.)

Example 6

Sunscreen Emulsion

| Dipropylene glycol | 5 |
| --- | --- |
| Xanthan gum | 0.1 |
| Bentonite | 1 |
| Stearic acid | 0.5 |
| Palmitic acid | 0.5 |
| Polyoxyethylene glyceryl ethylene isostearate | 1 |
| Glyceryl monostearate | 1 |
| Polyoxyethyleneglyceryl monostearate | 1 |
| Polyvinylpyrrolidone/eicosene copolymer | 1 |
| Tripropylene glycol dineopentanoate | 5 |
| Pentaerythritol tetra-2-ethylhexanoate | 2 |
| Isopropyl sebacate | 2 |
| Octocrylene | 5 |
| Bis ethylhexyloxyphenol methoxyphenyl triazine | 2 |
| Hexyl diethylaminohydroxybenzoylbenzoate | 2 |
| 4-tert butyl-4'-methoxybenzoylmethane | 2 |
| 2-ethylhexyl-paramethoxycinnamate | 5 |
| Ethylhexyl triazine | 0.5 |
| Sodium hexametaphosphage | 0.1 |

-continued

| EDTA-3Na | 0.1 |
| --- | --- |
| Triethanolamine | Appropriate amount |
| Preservative | Appropriate amount |
| Purified water | Balance |
| Perfume | Appropriate amount |

Example 7

Sunscreen Emulsion

| Glycerin | 5 |
| --- | --- |
| Xanthan gum | 0.3 |
| Smectone (from Kunimine Industries Co., Ltd.) | 0.5 |
| Stearic acid | 0.5 |
| Isostearic acid | 0.5 |
| Stearyl alcohol | 2 |
| Polyoxyethylene hydrogenated castor oil | 1 |
| Polyoxyethyleneglyceryl monostearate | 1 |
| Trimethylsiloxysilicic acid | 1 |
| Cyclomethicone | 3 |
| Caprylylmethicone | 3 |
| Cetyl ethylhexanoate | 10 |
| 2-ethyhexyl 2-ethylhexanoate | 3 |
| Octocrylene | 5 |
| Bis ethylhexyloxyphenol methoxyphenyl triazine | 2 |
| Hexyl diethylaminohydroxybenzoylbenzoate | 2 |
| 4-tert butyl-4'-methoxybenzoylmethane | 2 |
| Phenylbenzimidazolesulfonic acid | 1 |
| Ascorbic acid glucoside | 2 |

-continued

| EDTA-3Na | 0.1 |
| --- | --- |
| Potassium hydroxide | Appropriate amount |
| Preservative | Appropriate amount |
| Purified water | Balance |
| Perfume | Appropriate amount |

Example 8

Sunscreen Emulsion

| Alcohol | 5 |
| --- | --- |
| Dipropylene glycol | 5 |
| Xanthan gum | 0.1 |
| Bentonite | 1 |
| Glyceryl monostearate | 1 |
| Polyoxyethylene glycerin monoisostearate | 1 |
| Behenic acid | 1 |
| Behenyl alcohol | 2 |

-continued

| | |
|---|---|
| Trimethylsiloxysilicic acid | 1 |
| Cyclomethicone | 3 |
| Dimethicone | 2 |
| Isopropyl myristate | 5 |
| Octyl palmitate | 5 |
| Diethylhexyl succinate | 1 |
| Polyoxyethylene polyoxypropylene glycol | 1 |
| Octocrylene | 5 |
| Bis ethylhexyloxyphenol methoxyphenyl triazine | 2 |
| Hexyl diethylaminohydroxybenzoylbenzoate | 2 |
| 4-tert butyl-4'-methoxybenzoylmethane | 2 |
| Sodium hydroxymethoxybenzophenonesulfonate | 1 |
| Methylene bis-benzotriazolyl tetramethylbutylphenol | 2 |
| EDTA-3Na | 0.1 |
| Triethanolamine | Appropriate amount |
| Preservative | Appropriate amount |
| Purified water | Balance |
| Perfume | Appropriate amount |

INDUSTRIAL APPLICABILITY

The present invention can provide an oil-in-water emulsified composition that manifests a superior ultraviolet absorption effect and is superior in terms of the emulsification stability and the sensation during use. The oil-in-water emulsified composition of the present invention is preferably used as a sunscreen cosmetic.

The invention claimed is:

1. A storage-stable oil-in-water emulsified composition for ultraviolet protection comprising:
    (a) Octocrylene;
    (b) Bis ethylhexyloxyphenol methoxyphenyl triazine;
    (c) Hexyl diethylaminohydroxyhenzoylbenzoate;
    (d) 4-tert-butyl-4'-methoxybenzoylmethane;
    (e) Water soluble polymer;
    (f) Water-swelling clay mineral;
    (g) Oil component having IOB (ratio of Inorganic Value/Organic Value) of 0.05 or more, wherein the oil component is selected from the group consisting of isononyl isononanoate, glyceryl 2-ethylhexanoate, cetyl 2-ethylhexanoate and diisopropyl sebacate;
    (h) Higher fatty acid;
    (i) Surfactant; and
    (j) Water;
    wherein
    the octocrylene, bis ethylhexyloxyphenol methoxyphenyl triazine, hexyl diethylaminohydroxyhenzoylbenzoate and 4-tert-butyl-4'-methoxybenzoylmethane are dissolved in the oil phase of the emulsion.

2. The oil-in-water emulsified composition of claim 1, wherein the blend ratio of said water-swelling clay mineral is 0.01-4 mass % of the total amount of the oil-in-water emulsified composition.

3. The oil-in-water emulsified composition of claim 1, wherein the ratio of said oil component having IOB of 0.05 or more in the oil phase is 20-75 mass %.

4. The oil-in-water emulsified composition of claim 1, wherein said water soluble polymer is a polysaccharide.

5. The oil-in-water emulsified composition of claim 1, wherein the total blend ratio of (a) Octocrylene, (b) Bis ethylhexyloxyphenol methoxyphenyl triazine, (c) Hexyl diethylaminohydroxybenzoylbenzoate, and (d) 4-tert-butyl-4'-methoxybenzoylmethane is 5-30 mass % of the total amount of the oil-in-water emulsified composition.

6. The oil-in-water emulsified composition of claim 2, wherein the ratio of said oil component having IOB of 0.05 or more in the oil phase is 20-75 mass %.

7. The oil-in-water emulsified composition of claim 2, wherein said water soluble polymer is a polysaccharide.

8. The oil-in-water emulsified composition of claim 3, wherein said water soluble polymer is a polysaccharide.

9. The oil-in-water emulsified composition of claim 2, wherein the total blend ratio of (a) Octocrylene, (b) Bis ethylhexyloxyphenol methoxyphenyl triazine, (c) Hexyl diethylaminohydroxybenzoylbenzoate, and (d) 4-tert-butyl-4'-methoxybenzoylmethane is 5-30 mass % of the total amount of the oil-in-water emulsified composition.

10. The oil-in-water emulsified composition of claim 3, wherein the total blend ratio of (a) Octocrylene, (b) Bis ethylhexyloxyphenol methoxyphenyl triazine, (e) Hexyl diethylaminohydroxybenzoylbenzoate, and (d) 4-tert-butyl-4'-methoxybenzoylmethane is 5-30 mass % of the total amount of the oil-in-water emulsified composition.

11. The oil-in-water emulsified composition of claim 4, wherein the total blend ratio of (a) Octocrylene, (b) Bis ethylhexyloxyphenol methoxyphenyl triazine, (c) Hexyl diethylaminohydroxybenzoylbenzoate, and (d) 4-tert-butyl-4'-methoxybenzoylmethane is 5-30 mass % of the total amount of the oil-in-water emulsified composition.

12. A storage-stable oil-in-water emulsified sunscreen cosmetic composition for ultraviolet protection, said composition comprising:
    (a) Octocrylene;
    (b) Bis ethylhexyloxyphenol methoxyphenyl triazine;
    (c) Hexyl diethylaminohydroxyhenzoylbenzoate;
    (d) 4-tert-butyl-4'-methoxybenzoylmethane, wherein the total blend ratio of components (a), (b), (c) and (d) is 10-25 mass %;
    (e) Water soluble polymer;
    (f) Water-swelling clay mineral;
    (g) Oil component having IOB of 0.05 or more, wherein the oil component is selected from the group consisting of isononyl isononanoate, glyceryl 2-ethylhexanoate, cetyl 2-ethylhexanoate and diisopropyl sebacate;
    (h) Higher fatty acid;
    (i) Surfactant; and
    (j) Water;
    wherein the octocrylene, bis ethylhexyloxyphenol methoxyphenyl triazine, hexyl diethylaminohydroxyhenzoylbenzoate and 4-tert-butyl-4'-methoxybenzoylmethane are dissolved in the oil phase of the emulsion.

13. A storage-stable oil-in-water emulsified sunscreen cosmetic composition for ultraviolet protection, said composition comprising:
    (a) Octocrylene;
    (b) Bis ethylhexyloxyphenol methoxyphenyl triazine;
    (c) Hexyl diethylaminohydroxyhenzoylbenzoate;
    (d) 4-tert-butyl-4'-methoxybenzoylmethane, wherein the total blend ratio of components (a), (b), (c) and (d) is 10-25 mass %;
    (e) 0.01-5 mass % water soluble polymer;
    (f) 0.01-4 mass % water-swelling clay mineral;
    (g) 20-75 mass % oil component having IOB of 0.05 or more, wherein the oil component is selected from the group consisting of isononyl isononanoate, glyceryl 2-ethylhexanoate, cetyl 2-ethylhexanoate and diisopropyl sebacate;
    (h) 0.01-10 mass % higher fatty acid;
    (i) 0.01-10 mass % surfactant; and
    (j) Water;

wherein all amounts are based on the total amount of the oil-in-water emulsified composition and wherein the octocrylene, bis ethylhexyloxyphenol methoxyphenyl triazine, hexyl diethylaminohydroxyhenzoylbenzoate and 4-tert-butyl-4'-methoxybenzoylmethane are dissolved in the oil phase of the emulsion.

14. The oil-in-water emulsified composition of claim 13 wherein said water soluble polymer is a polysaccharide.

* * * * *